(12) United States Patent
Palmaz et al.

(10) Patent No.: US 9,399,087 B2
(45) Date of Patent: Jul. 26, 2016

(54) IMPLANTABLE MATERIALS HAVING ENGINEERED SURFACES COMPRISING A PATTERN OF FEATURES AND METHOD OF MAKING SAME

(71) Applicant: ADVANCED BIO PROSTHETIC SURFACES, LTD., a wholly owned subsidiary of Palmaz Scientific, Inc., Dallas, TX (US)

(72) Inventors: Julio C. Palmaz, Napa, CA (US); Eugene A. Sprague, San Antonio, TX (US)

(73) Assignee: Advanced Bio Prosthetic Surfaces, Ltd., a wholly owned subsidiary of Palmaz Scientific, Inc., Fremont, CA (US)

( * ) Notice: Subject to any disclaimer, the term of this patent is extended or adjusted under 35 U.S.C. 154(b) by 0 days.

(21) Appl. No.: 14/256,674

(22) Filed: Apr. 18, 2014

(65) Prior Publication Data

US 2014/0314992 A1  Oct. 23, 2014

Related U.S. Application Data

(60) Division of application No. 13/168,897, filed on Jun. 24, 2011, now Pat. No. 8,709,066, which is a continuation of application No. 11/091,669, filed on Mar. 28, 2005, now Pat. No. 8,147,859, which is a continuation of application No. PCT/US03/30383, filed on Sep. 26, 2003.

(60) Provisional application No. 60/414,031, filed on Sep. 26, 2002.

(51) Int. Cl.
| | |
|---|---|
| A61F 2/06 | (2013.01) |
| A61L 31/02 | (2006.01) |
| A61F 2/00 | (2006.01) |
| A61F 2/02 | (2006.01) |

(52) U.S. Cl.
CPC ............... *A61L 31/028* (2013.01); *A61F 2/00* (2013.01); *A61F 2/0077* (2013.01); *A61F 2/02* (2013.01); *A61L 31/022* (2013.01); *A61L 31/024* (2013.01); *A61F 2002/0086* (2013.01); *A61F 2310/00616* (2013.01); *Y10T 428/24355* (2015.01)

(58) Field of Classification Search
CPC .......................................................... A61F 2/06
See application file for complete search history.

(56) References Cited

U.S. PATENT DOCUMENTS

2001/0001834 A1 * 5/2001 Palmaz .................... A61F 2/82
623/1.15

* cited by examiner

*Primary Examiner* — Rosanne Kosson
(74) *Attorney, Agent, or Firm* — David G. Rosenbaum; J. Peter Paredes; Rosenbaum IP, P.C.

(57) ABSTRACT

Implantable materials having defined patterns of affinity regions for binding endothelial cells and providing for directed endothelial cell migration across the surface of the material. The affinity regions include photochemically altered regions of a material surface and physical members patterned on the material surface that exhibit a greater affinity for endothelial cell binding and migration than the remaining regions of the material surface.

19 Claims, 6 Drawing Sheets

IMPLANTABLE MATERIALS HAVING ENGINEERED SURFACES COMPRISING A PATTERN OF FEATURES AND METHOD OF MAKING SAME

CROSS-REFERENCE TO RELATED INVENTIONS

This application is a divisional of application U.S. Ser. No. 13/168,897, filed Jun. 24, 2011; which is a continuation of application U.S. Ser. No. 11/091,669, filed Mar. 28, 2005, now U.S. Pat. No. 8,147,859; which is a continuation of International Application No. PCT/US2003/030383 filed Sep. 26, 2003 (International Publication No. WO 2004/028347), which claims priority to Provisional Application Ser. No. 60/414,031 filed Sep. 26, 2002, all herein incorporated by reference in their entireties.

BACKGROUND OF THE INVENTION

The present invention relates generally to implantable medical devices and more particularly to controlling surface properties of implantable biocompatible materials suitable for fabrication of implantable medical devices. Implantable medical devices are fabricated of materials that are sub-optimal in terms of the biological response they elicit in vivo. Many conventional materials used to fabricate implantable devices, such as titanium, polytetrafluoroethylene, silicone, carbon fiber and polyester, are used because of their strength and physiologically inert characteristics. However, tissue integration onto these materials is typically slow and inadequate. Certain materials, such as silicone and polyester, elicit a significant inflammatory, foreign body response that drives fibrous encapsulation of the synthetic material. The fibrous encapsulation may have significant adverse effects on the implant. Moreover, conventional biomaterials have proved inadequate in eliciting a sufficient healing response necessary for complete device integration into the body. For example, in devices that contact blood, such as stents and vascular grafts, attempts to modify such devices to promote endothelial cell adhesion may have a concomitant effect of making the devices more thrombogenic.

When implanted, conventional blood-contacting implantable devices, such as stents, stent-grafts, grafts, valves, shunts and patches, fail to develop a complete endothelial layer, thereby exposing the device material to thrombus formation or smooth muscle cell proliferation, and ultimate failure of the implanted device. It has been recognized that, when implanted into the body, metals are generally considered to have superior biocompatibility than polymers used to fabricate commercially available polymeric grafts.

In investigating cellular interactions with prosthetic material surfaces, it has been found that cell adhesion to the material surface is mediated by integrins present on cell membranes that interact with the prosthetic surface. Integrins are the most prominent member of a class of extracellular matrix (ECM) adhesion receptors. Integrins are a large family of heterodimeric transmembrane proteins with different $\alpha$ and $\beta$ subunits. Integrins are regulated at several levels. Modulation of the affinity of the adhesion receptor for ligand, termed affinity modulation, is a mechanism for activation of platelet aggregation and is believed to underlie activation of leukocyte adhesion. Adhesive strengthening by clustering of adhesion receptors or by cytoskeletal-dependent processes such as cell spreading has been shown to be crucial for strong cellular attachment, control of cell growth and cell motility. Under high shear forces present in flowing blood, leukocytes first tether, then roll along the vessel surface. When a local signal, e.g., a cytokine, is released in their vicinity, the leukocyte arrests, develops a firm adhesion then migrates across the endothelium. Tethering, rolling, arrest and adhesion tightening are all known to result from activation of leukocyte integrins.

Once adhered to a surface, cell spreading and migration are associated with assembly of focal adhesion junctions. Cell migration entails the coordination of cytoskeletal-mediated process extension, i.e., filopodia and lamellopodia, formation of adhesive contacts at the leading edge of a cell, breaking adhesive contacts, and cytoskeletal retraction at the trailing edge of the cell. Focal adhesions are comprised of integrins as the major adhesion receptors along with associated cytoplasmic plaque proteins. Assembly of focal adhesions is regulated by extracellular ligand binding events and by intracellular signaling events. Ligand binding controls localization of $\beta 1$- and $\beta 3$-containing integrins into focal adhesions. The cytoplasmic domains of the $\beta$ subunits have intrinsic signals for focal adhesion localization, but incorporation of the integrins into focal adhesions is prevented by the a subunits of the heterodimers. Ligand binding, however, relieves this inhibition and allows the subunit cytoplasmic tail signals to recruit the integrin dimmer into the focal adhesion.

Attempts at coating implanted metal devices, such as stents, with proteins that contain the Arg-Gly-Asp (RGD) attachment site have been made with some success. The RGD sequence is the cell attachment site of a large number of adhesive extracellular matrix, blood, and cell surface proteins and many of the known integrins recognize the RGD sequence in their adhesion protein ligands. Integrin-binding activity may also be reproduced by synthetic peptides containing the RGD sequence. However, bare metal implanted materials will not, of course, have native RGD attachment sites. Thus, metal implantable devices, such as stents, have been derivitized with polymers having RGD attachment sites bound to the polymer matrix.

It has been found that when prosthetic materials are implanted, integrin receptors on cell surfaces interact with the prosthetic surface. When cells come into contact with the extracellular matrix, such as a prosthetic surface, their usual response is to extend filopodia, and integrins at the tip of the filopodia bind to the extracellular matrix and initiate the formation of focal adhesions. Actin-rich lamellipodia are generated, often between filopodia, as the cell spreads on the extracellular matrix. Fully developed focal adhesions and associated actin stress fibers ensue. These same evens occur during cell migration as cells extend lamellipodia and form focal adhesions to derive the traction necessary for movement. Giancotti, F. G., et al. *Science,* 285:13 Aug. 1999, 1028-1032.

The integrin receptors are specific for certain ligands in vivo. If a specific protein is adsorbed on a prosthetic surface and the ligand exposed, cellular binding to the prosthetic surface may occur by integrin-ligand docking. It has also been observed that proteins bind to metals in a more permanent fashion than they do to polymers, thereby providing a more stable adhesive surface. The conformation of proteins coupled to surfaces of most medical metals and alloys appears to expose greater numbers of ligands and attract endothelial cells having surface integrin clusters to the metal or alloy surface, preferentially over leukocytes.

Because of their greater adhesive surface profiles, metals are also susceptible to short-term platelet activity and/or thrombogenicity. These deleterious properties may be offset by administration of pharmacologically active antithrombogenic agents in routine use today. Surface thrombogenicity usually disappears 1-3 weeks after initial exposure. Antithrombotic coverage is routinely provided during this period of time for coronary stenting. In non-vascular applications such as musculoskeletal and dental, metals have also greater tissue compatibility than polymers because of similar molecular considerations. The best article to demonstrate the fact that all polymers are inferior to metals is van der Giessen, W J. et al. *Marked inflammatory sequelae to implantation of biodegradable and non-biodegradable polymers in porcine coronary arteries*, Circulation, 1996:94(7):1690-7.

Normally, endothelial cells (EC) migrate and proliferate to cover denuded areas until confluence is achieved. Migration, quantitatively more important than proliferation, proceeds under normal blood flow roughly at a rate of 25 µm/hr or about 2.5 times the diameter of an EC, which is nominally 10 µm. EC migrate by a rolling motion of the cell membrane, coordinated by a complex system of intracellular filaments attached to clusters of cell membrane integrin receptors, specifically focal contact points. The integrins within the focal contact sites are expressed according to complex signaling mechanisms and eventually couple to specific amino acid sequences in substrate adhesion molecules. An EC has roughly 16-22% of its cell surface represented by integrin clusters. Davies, P. F., Robotewskyi A., Griem M. L. *Endothelial cell adhesion in real time*. J. Clin. Invest. 1993; 91:2640-2652, Davies, P. F., Robotewski, A., Griem, M. L., *Qualitiative studies of endothelial cell adhesion*, J. Clin. Invest. 1994; 93:2031-2038. This is a dynamic process, which involves more than 50% remodeling in 30 minutes. The focal adhesion contacts vary in size and distribution, but 80% of them measure less than 6 $\mu m^2$, with the majority of them being about 1 $\mu m^2$, and tend to elongate in the direction of flow and concentrate at leading edges of the cell. Although the process of recognition and signaling to determine specific attachment receptor response to attachment sites is not completely understood, availability of attachment sites will favorably influence attachment and migration. It is known that materials commonly used as medical grafts, such as polymers, do not become covered with EC and therefore do not heal after they are placed in the arteries. It is therefore an object of this invention to replace polymer grafts with metal grafts that can potentially become covered with EC and can heal completely. Furthermore, heterogeneities of materials in contact with blood flow are preferably controlled by using vacuum deposited materials.

There have been numerous attempts to increase endothelialization of implanted medical devices such as stents, including covering the stent with a polymeric material (U.S. Pat. No. 5,897,911), imparting a diamond-like carbon coating onto the stent (U.S. Pat. No. 5,725,573), covalently binding hydrophobic moieties to a heparin molecule (U.S. Pat. No. 5,955,588), coating a stent with a layer of blue to black zirconium oxide or zirconium nitride (U.S. Pat. No. 5,649,951), coating a stent with a layer of turbostratic carbon (U.S. Pat. No. 5,387,247), coating the tissue-contacting surface of a stent with a thin layer of a Group VB metal (U.S. Pat. No. 5,607,463), imparting a porous coating of titanium or of a titanium alloy, such as Ti—Nb—Zr alloy, onto the surface of a stent (U.S. Pat. No. 5,690,670), coating the stent, under ultrasonic conditions, with a synthetic or biological, active or inactive agent, such as heparin, endothelium derived growth factor, vascular growth factors, silicone, polyurethane, or polytetrafluoroethylene (U.S. Pat. No. 5,891,507), coating a stent with a silane compound with vinyl functionality, then forming a graft polymer by polymerization with the vinyl groups of the silane compound (U.S. Pat. No. 5,782,908), grafting monomers, oligomers or polymers onto the surface of a stent using infrared radiation, microwave radiation or high voltage polymerization to impart the property of the monomer, oligomer or polymer to the stent (U.S. Pat. No. 5,932,299). However, all these approaches do not address the lack of endothelialization of polymer grafts.

In accordance with the present invention, the capacity for complete endothelialization of conventional implantable materials, including metals and polymers, may be enhanced by imparting a pattern of chemically and/or physiochemically active features onto a blood contacting surface of the implantable material. The inventive implantable metal devices may be fabricated of polymers, pre-existing conventional wrought metallic materials, such as stainless steel or nitinol hypotubes, or may be fabricated by thin film vacuum deposition techniques. In accordance with the present invention, it is preferable to fabricate the inventive implantable materials and resulting devices by vacuum deposition of either or both of the base implant material and the chemically and/or physiochemically active features. Vacuum deposition permits greater control over many material characteristics and properties of the resulting material and formed device. For example, vacuum deposition permits control over grain size, grain phase, grain material composition, bulk material composition, surface topography, mechanical properties, such as transition temperatures in the case of a shape memory alloy. Moreover, vacuum deposition processes will permit creation of devices with greater material purity without the introduction of large quantities of contaminants that adversely affect the material and, therefore, the mechanical and/or biological properties of the implanted device. Vacuum deposition techniques also lend themselves to fabrication of more complex devices than those that are manufactured by conventional cold-working techniques. For example, multi-layer structures, complex geometrical configurations, extremely fine control over material tolerances, such as thickness or surface uniformity, are all advantages of vacuum deposition processing.

In vacuum deposition technologies, materials are formed directly in the desired geometry, e.g., planar, tubular, etc. The common principle of vacuum deposition processes is to take a material in a minimally processed form, such as pellets or thick foils, known as the source material and atomize them. Atomization may be carried out using heat, as is the case in physical vapor deposition, or using the effect of collisional processes, as in the case of sputter deposition, for example. In some forms of deposition a process such as laser ablation, which creates microparticles that typically consist of one or more atoms, may replace atomization; the number of atoms per particle may be in the thousands or more. The atoms or particles of the source material are then deposited on a substrate or mandrel to directly form the desired object. In other deposition methodologies, chemical reactions between ambient gas introduced into the vacuum chamber, i.e., the gas source, and the deposited atoms and/or particles are part of the deposition process. The deposited material includes compound species that are formed due to the reaction of the solid source and the gas source, such as in the case of chemical vapor deposition. In most cases, the deposited material is then either partially or completely removed from the substrate, to form the desired product.

A first advantage of vacuum deposition processing is that vacuum deposition of the metallic and/or pseudometallic films permits tight process control and films may be deposited that have a regular, homogeneous atomic and molecular pattern of distribution along their fluid-contacting surfaces. This avoids the marked variations in surface composition, creating predictable oxidation and organic adsorption patterns and has predictable interactions with water, electrolytes, proteins and cells. In particular, EC migration is supported by a homogeneous distribution of binding domains that serve as natural or implanted cell attachment sites in order to promote unimpeded migration and attachment.

Secondly, in addition to materials and devices that are made of a single metal or metal alloy layer, the inventive grafts may be comprised of a layer of biocompatible material or of a plurality of layers of biocompatible materials formed upon one another into a self-supporting multilayer structure because multilayer structures are generally known to increase the mechanical strength of sheet materials, or to provide special qualities by including layers that have special properties such as superelasticity, shape memory, radio-opacity, corrosion resistance etc. A special advantage of vacuum deposition technologies is that it is possible to deposit layered materials and thus films possessing exceptional qualities may be produced (cf., H. Holleck, V. Schier: *Multilayer PVD coatings for wear protection*, Surface and Coatings Technology, Vol. 76-77 (1995) pp. 328-336). Layered materials, such as superstructures or multilayers, are commonly deposited to take advantage of some chemical, electronic, or optical property of the material as a coating; a common example is an antireflective coating on an optical lens. Multilayers are also used in the field of thin film fabrication to increase the mechanical properties of the thin film, specifically hardness and toughness.

Thirdly, the design possibilities for possible configurations and applications of the inventive graft are greatly realized by employing vacuum deposition technologies. Specifically, vacuum deposition is an additive technique that lends itself toward fabrication of substantially uniformly thin materials with potentially complex three dimensional geometries and structures that cannot be cost-effectively achieved, or in some cases achieved at all, by employing conventional wrought fabrication techniques. Conventional wrought metal fabrication techniques may entail smelting, hot working, cold working, heat treatment, high temperature annealing, precipitation annealing, grinding, ablation, wet etching, dry etching, cutting and welding. All of these processing steps have disadvantages including contamination, material property degradation, ultimate achievable configurations, dimensions and tolerances, biocompatibility and cost. For example conventional wrought processes are not suitable for fabricating tubes having diameters greater than about 20 mm, nor are such processes suitable for fabricating materials having wall thicknesses down to about 1 μm with sub-μm tolerances.

Overall rate to reach confluence for the endothelial cells on the blood contact surface of implanted medical device is mainly determined by two factors, the rate of cell movement and rate of cell proliferation, with the first being more important. The rate of cell movement further comprises three interrelated steps. Initially, a cell forms lamellipodia and flopodia that protrude outward. This step involves reassembly of actins in the forefront of lambaepolia. After protrusion of lamellipodia from one or multiple points from the cell membrane, the front end of the lamellipodia will form a close attachment, called focal adhesion point, to the substratum through the interaction of integrin on the cell membrane and extracellular matrix binding site. The final step of cell movement involves the contraction of the posterior end through the action of myosin II. The formation of a focal adhesion point is critical for the cell movement because the protruding lamellipodia will otherwise fold back. Without the tension force from the focal adhesion point, a cell loses the contraction from the posterior end and hence stops moving.

Availability of attachment sites on the substratum is not only important for the focal adhesion point formation, but also important for propagation. It has been shown that cells are forced to spread, survive better and proliferate faster than cells that are confined to the same amount of surface area (*Science* 276:1425-1428, 1997). This may explain why spreading of neighbor cells stimulate a cell to proliferate, after cells are lost from epithelium.

The formation of extracellular matrix (ECM) is, to much extent, determined by the cells within it because molecules which form ECM are secreted by the cells. Subsequently, the structure of the ECM, and hence the distribution of attachment sites on the ECM for the integrin binding, determines the focal adhesion point formation, the critical step in cell movement. Therefore, proper distribution of integrin binding sites on the surface of an implanted medical device substantially determines the speed of reendothelialization from the ends surrounding the device.

There still remains a need for a medical device that stimulates endothelial proliferation and movement when implanted in order to form an endothelial layer over the medical device. Furthermore, there is a remaining need for a method of fabricating such a medical device.

SUMMARY OF THE INVENTION

In accordance with an aspect of the present invention, there is provided an implantable material having at least one blood contact surface comprising an evenly distributed geometric feature for cell attachment. The evenly distributed feature on the blood contact surface of the medical device includes: circle dots, square dots, rectangular dots, triangle dots, parallel lines and intersecting lines, or any combination thereof. Additionally, another aspect of the present invention provides methods of making a device that has evenly distributed geometric features on the blood contact surface.

DETAILED DESCRIPTION OF THE PREFERRED EMBODIMENTS

The present inventions takes advantage of the discovered relationship between chemically or physiochemically-active geometric features defined and distributed on a blood contact surface enhanced endothelial cell binding, proliferation and migration over the blood contact surface of the implantable material. The present invention involves focal adhesion point formation during cellular movement and the well-established observation known as anchorage dependence, that spreading cells proliferate faster than non-spreading cells. It has been found the addition of a patterned array of ultra-thin features having a hydrophobic, hydrophilic or surface energy difference relative to the surface onto which the ultra-thin features are added, enhances the binding, proliferation and migration of endothelial cells to and between the features and across the surface. Use of the term "ultra-thin" is intended to include material thicknesses between about 0.1 μm and 3 μm. It has been found that below about 3 μm the interactions between endothelial cells and the ultra-thin features is primarily chemical and electrochemical. Features having thicknesses greater than 3 μm and up to about 20 μm may also be employed in the present invention, it being understood that as the thickness of the feature increases there is a decreasing chemical and/or electrochemical interaction between the feature and the endothelial cells and an increasing physical interaction.

Additionally, it has been found that by employing UV irradiation to oxidized titanium or titanium-alloy surfaces, photochemical alteration of the surface titanium oxides alter the hydrophobicity of the exposed titanium oxides and act as affinity binding and migration sites for endothelial cell attachment and proliferation across a titanium or titanium-alloy surface. Where UV irradiation is employed, the thickness of the photochemically altered regions of titanium oxide are, for all practical purposes, 0 μm. Thus, within the context of the present application, the term "geometric features" is intended to include both physical members and photochemically-altered regions having thicknesses having thicknesses down to 0 μm.

Figure 1:
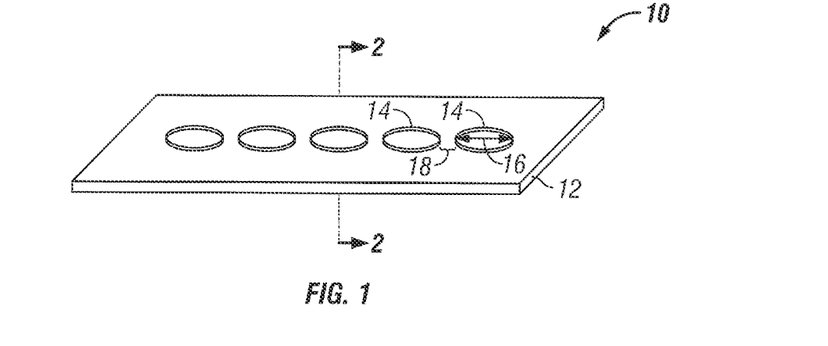
FIG. 1 is a perspective view of an embodiment of the present invention including evenly distributed elevated geometric features on the surface of an implantable material.

In FIG. 1, a portion of an implantable material 10 showing the surface material 12 with described elevated geometric features 14 is illustrated. The geometric features are elevated from the surface of the implantable material to a height ranging from about sub-micron to about 20 μm. Preferably, the height of the geometric feature 14 ranges from about sub-micron to about 3 μm. The shape of geometric features can be either circular, square, rectangle, triangle, parallel lines, straight or curvilinear lines or any combination thereof. Each of the geometric features is preferably from about 10 μm to about 75 μm, and preferably from about 15 μm to 50 μm in feature width 16, or feature diameter if the geometric feature is circular. A gap distance 18 between each of the geometric features should generally be the same as the feature width 16, i.e., between about 10 μm to about 75 μm edge-to-edge.

Figure 2:
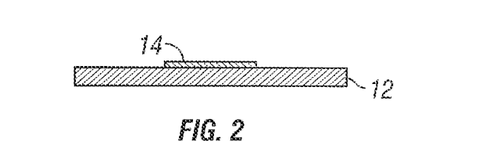
FIG. 2 is cross-sectional view of FIG. 1 along line 2-2.

FIG. 2 is a cross-sectional view along line 2-2 in FIG. 1. One of the elevated geometric features 14 is shown on the surface 12 of the implantable material.

Figure 3:
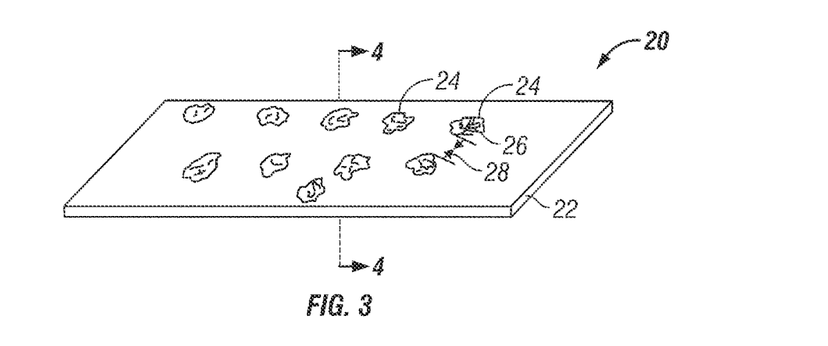
FIG. 3 is a perspective view of an embodiment of the present invention including evenly distributed chemically defined geometric features on the surface of an implantable material.

In FIG. 3, a titanium or titanium-alloy material 20 is heating to oxidize and form titanium dioxide on the surface of the material 20, then features 24 are formed by exposing the material 20 to UV through a pattern mask. UV irradiation alters the titanium oxides in the areas of features 24, thereby chemically altering the geometric features 24 relative to the surrounding the surrounding surface area 22 of material 20. The shape of geometric features can be circular, square, rectangle, triangle, parallel lines, intersecting lines or any combination. Each of the geometric features is from about 10 μm to about 75 μm, and preferably from about 15 μm to 50 μm in feature width 16, or feature diameter if the geometric feature is circular. The gap distance 28 between each component of the geometric features is in the same magnitude as the feature width 26.

Figure 4:
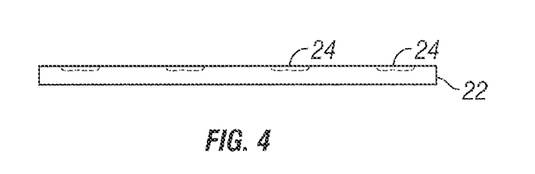
FIG. 4 is a cross-sectional view of FIG. 3 along line 4-4.

FIG. 4 is a cross-sectional view of FIG. 3 along line 4-4. The described geometric features 24 are indicated by the dotted lines, which indicates that the geometric features 24 are at the same level of the surrounding surface 22.

Figure 5:
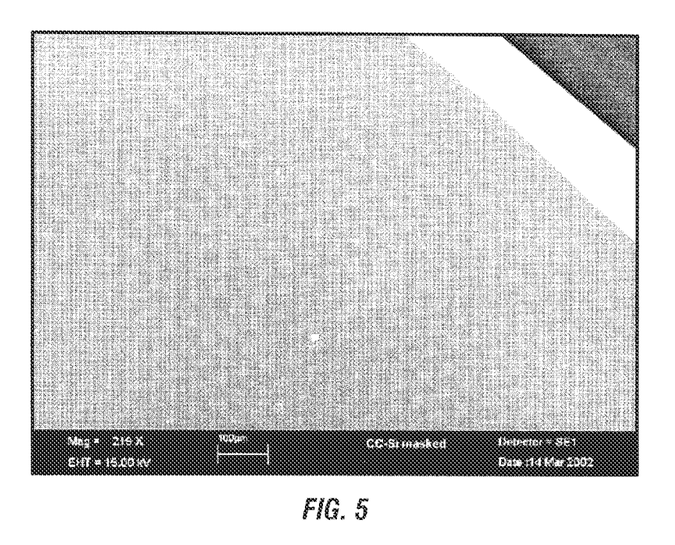
FIG. 5 is a photomicrograph showing an embodiment of the present invention including geometric features as carbon coated silicon.

FIG. 5 shows geometric features that are evenly distributed across the at least one surface of the implantable material that contacts body fluid, preferably blood. As disclosed in FIG. 1 and FIG. 2, the geometric features are elevated from the rest of the surface to a height ranging from about sub-micron to about 20 micrometer. Preferably, the height of the geometric feature ranges from about sub-micron to about 3 micrometer. The shape of the geometric features is not confined within the shape that is shown. The shape of the chemically defined domain can also be any of circle, square, rectangle, triangle, parallel lines, intersecting lines or any combination of the above.

Figure 6A:
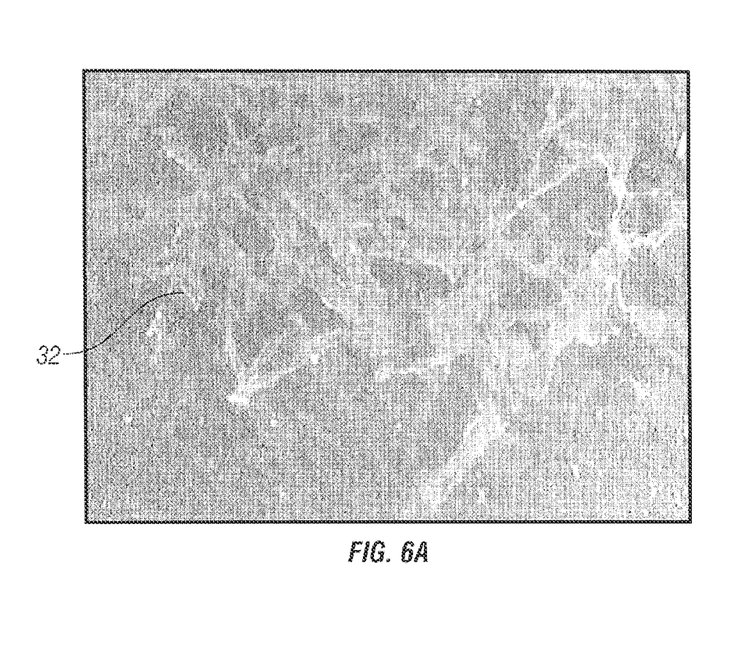
FIGS. 6*a*-6*c* are photomicrographs showing cellular migration on the surface with no inventive geometric features versus on the surface with inventive features.
Figure 6B:
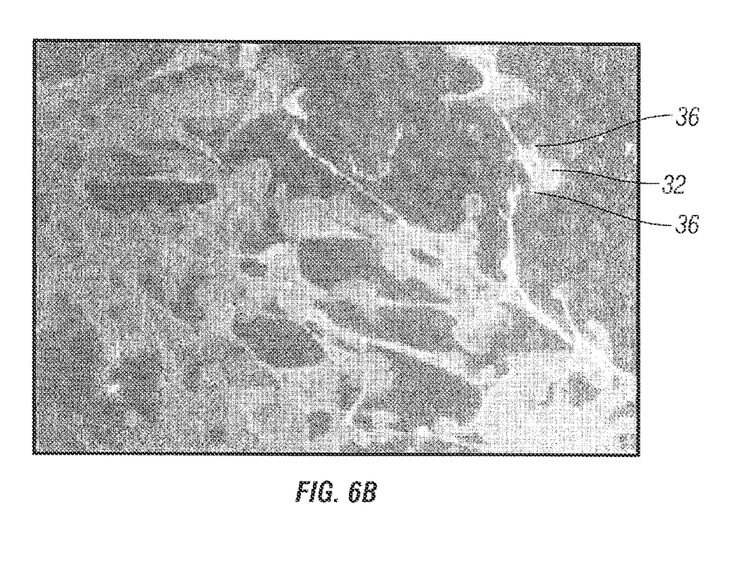

FIG. 6A shows the cell 32 spreading on the surface of hydrophilic treated Si. FIG. 6B shows the cell 32 spreading on the surface of hydrophilic treated Si with circular dots that are 15 microns in diameter. Cells in FIG. 6B appear to have much more focal adhesion points 36 than those in FIG. 6A. Because these geometric features provide for cell attachment, acting as affinity domains, the size of each of these affinity domains relative to the size of an endothelial cell determines the availability of affinity domains to the subsequent round of cell movement. According to the present invention, the preferred size of each of the individual component of the geometric features is about 10 μm to about 75 μm, and preferably from about 15 μm to 50 μm in feature width, or diameter if the geometric feature is circular. As described in the background section, focal adhesion point formation is the critical step in cell movement and cell proliferation, therefore, geometric features such as carbon dots on the hydrophilic Si surface promote cell movement. It is known to the person skilled in the art that spreading of cells promotes cell proliferation. Promoting cell movement and cell proliferation ultimately accelerates covering of the implanted implantable material with endothelial cells on exposed surfaces having the geometric features. Although the geometric features shown in FIG. 6B are circular, the shape of the geometric features are not limited to this particular embodiment.

Figure 6C:
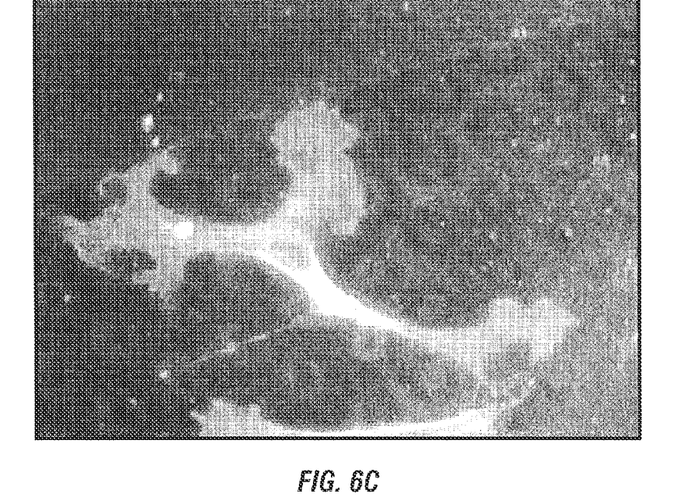

FIG. 6C is a magnification of a portion of the image of FIG. 6B. Multiple focal adhesion points 36 are again shown. Wide spreading of the cell is primarily due to the formation of multiple focal adhesion points on the circular geometric features. Extensive spreading of the cells is beneficial towards endothelialization because it promotes cell movement and cell proliferation.

Figure 7:
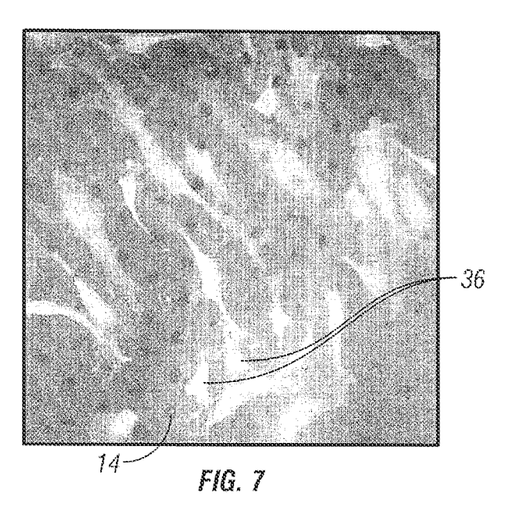
FIG. 7 is a photomicrograph showing the stained focal adhesion points close to the geometric features.

FIG. 7 shows the stained focal adhesion points 36 of human aotic endothelial cells (HAEC) on the surface of an implantable material with geometric features 14 that are in the form of carbon dots. The focal adhesion points are located at or very close to the geometric features 14. As described in the background section, these focal adhesion points serve as tension points for the cell to contract from the opposite end of the cell and hence promote cell movement.

Figure 8A:
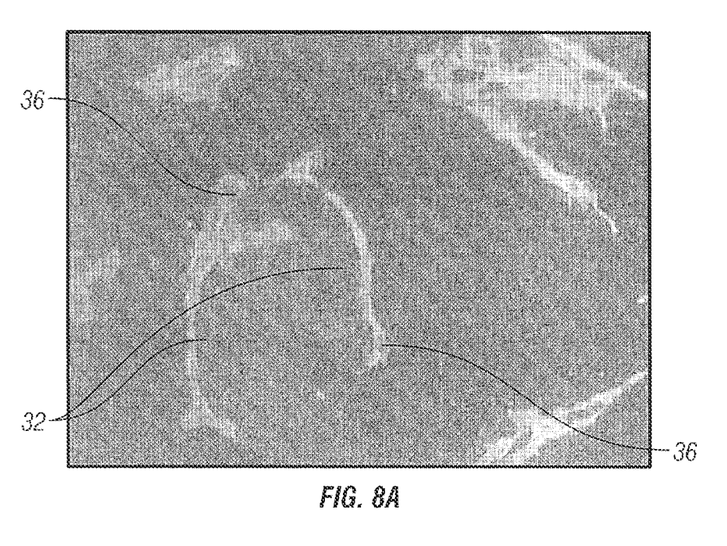
FIGS. 8*a*-8*b* are photomicrographs showing the formation of multiple focal adhesion points of a migrating cell and its attachment to the inventive geometric features.

FIG. 8A shows the wide spreading of cells 32 and focal multiple focal adhesion points 36 on the surface of an implantable material with geometric features that are in the form of NiTi dots of 25 micrometers in diameter. The NiTi dots are invisible due to the weak contrast between the NiTi dots and surrounding Si surface.

Figure 8B:
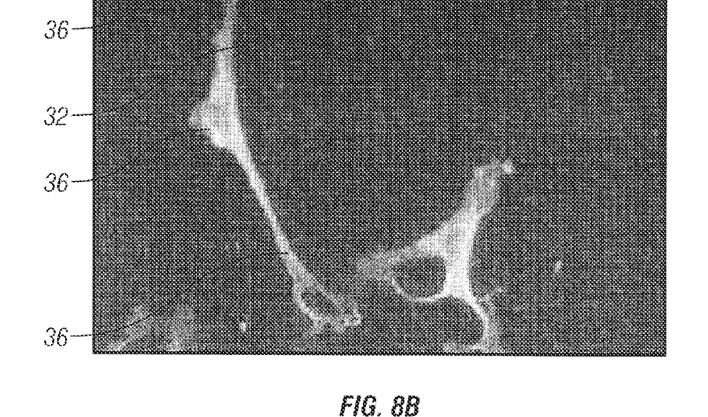

FIG. 8B shows a magnified slide of a human aotic epithelial cell 32, as shown in FIG. 8A. Multiple focal adhesion points 36 are shown to encapsulate the NiTi dots patterned on the hydrophilic Si surface.

Figure 9A:
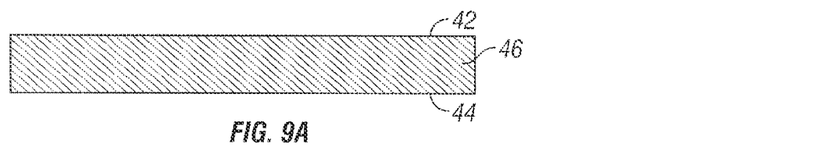
FIGS. 9*a*-9*d* are cross-sectional diagrammatic views of an embodiment of the present invention, the combination of a-d representing the steps to make an inventive implantable material with elevated geometric features.

Referring to FIG. 9A, a portion of an implantable material 46 with surface 42 and 44 is shown.

Figure 9B:
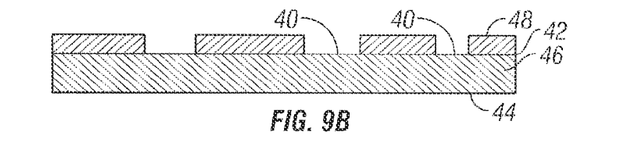

Referring to FIG. 9B, according to the present invention, a machined mask 48 having laser-cut holes 40 of defined size ranging from about 10 μm to about 75 μm, and preferably from about 15 μm to 50 μm, patterned throughout coats at least one surface 42 of the implantable material 46 and is tightly adhered to the covered surface 42.

Figure 9C:
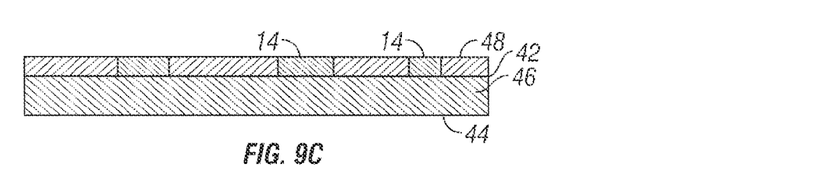

Referring to FIG. 9C, a thin film of material 14 was deposited into the space as defined by the holes 40, as seen in FIG. 9B, in the mask 48 by thin film deposition procedures.

Figure 9D:
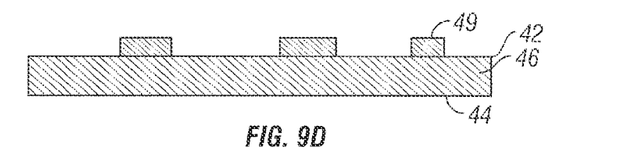

Referring to FIG. 9D, after deposition, the mask is removed to reveal the geometric features 49 patterned across the at least one surface 42 of the implantable material 46.

As described above, the shape of the holes in the mask could be in any of the shapes described for the geometric features including: circle, square, rectangle, triangle, parallel lines and intersecting lines, or any combination thereof. In the thin film deposition embodiment of the manufacturing the geometric features, the geometric features are elevated from the surface of the implantable material. The thickness of the geometric features is based upon the thickness of the holes in the mask, the thickness ranging from about sub-micron to about 20 micrometer. Preferably, the thickness of the holes in the mask range from about sub-micron to about 3 micrometer.

In accordance with an alternate embodiment of the present invention, the substrate for the implantable medical device is formed of titanium, nickel-titanium alloy or other titanium-rich alloy metals, which is oxidized to convert surface titanium to titanium dioxide, then covered with a pattern-mask and exposed to high intensity UV irradiation. It is well-known that titanium dioxide ($TiO_2$) absorbs UV radiation and has been used in a variety of applications as a UV inhibitor to prevent UV transmission across a $TiO_2$ barrier layer. It has been discovered that upon exposure to UV irradiation, an originally hydrophobic and oleophilic titanium oxide layer becomes amphiphilic. The effect of UV irradiation on a titanium oxide surface is believed to occur because of unsymmetrial cleavage of the Ti—O bond to leave $Ti^{3+}$ ions on the surface in some regions. Presently, these amphiphilic surfaces are being used in a range of technological applications, such as self-cleaning paints and anti-misting glasses. It has been recognized that these amphiphilic titanium oxide layers have use in medical applications. Zarbakhsh, A., *Characterization of photon-controlled titanium oxide surfaces*, ISIS Experimental Report, Rutherford Appelton Laboratory, May 16, 2000 (which may be found on the internet at: www.isis.rl.ac.uk/isis2001/reports/11144.pdf).

It has been recognized by the present inventors that the amphiphilic state of the UV irradiated titanium oxide may be advantageously employed as an alternative to depositing patterned features onto the implantable substrate surface. An implantable substrate fabricated of titanium or a titanium alloy is masked with a pattern mask having a plurality of openings passing there through. As with the above-described embodiment, the plurality of openings preferably have a size and special array selected to define affinity binding domains and cellular migration cites for promoting endothelial cell binding and proliferation across the substrate surface. The open surface area of each of the plurality of openings in the pattern mask is preferably in the range of between about 10 to 75 μm, and with adjacent pairs of openings being in a spaced apart relationship such that a distance of about 10 to about 75 μm exists between the openings, the inter-opening distance corresponding to the size of the opening. By interposing the pattern mask between a UV source and the substrate surface, a pattern of UV irradiated regions is imparted to the substrate surface, thereby altering the titanium dioxides present at the irradiated regions and forming affinity domains at the substrate surface.

Figure 10A:
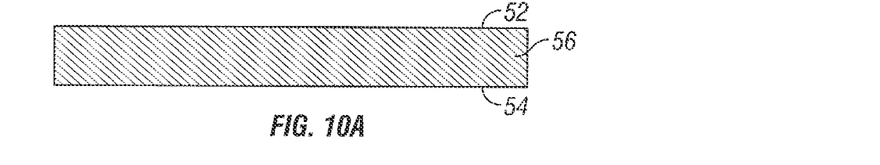
FIGS. 10*a*-10*d* are cross-sectional diagrammatic views of an embodiment of the present invention, the combination of a-d representing the steps to make an inventive implantable material with chemically defined geometric features.

Referring to FIG. 10A, a portion of an implantable material 56 made of titanium or a titanium-alloy is shown having at least one surface 52 and 54 that is oxidized by heating or an equivalent known by the person skilled in the art.

Figure 10B:
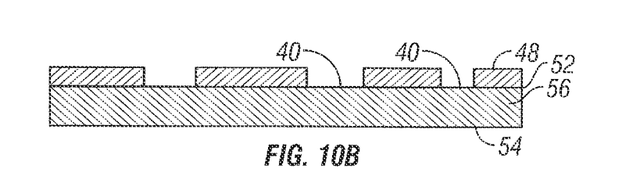

Referring to FIG. 10B, according to the present invention, a machined mask 48 that had laser-cut holes 40 of defined size from 10 μm to about 75 μm, and preferably from about 15 μm to 50 μm, patterned throughout to coat the at least one surface 52 of the implantable material 56 and is tightly adhered to the covered surface 52.

Figure 10C:
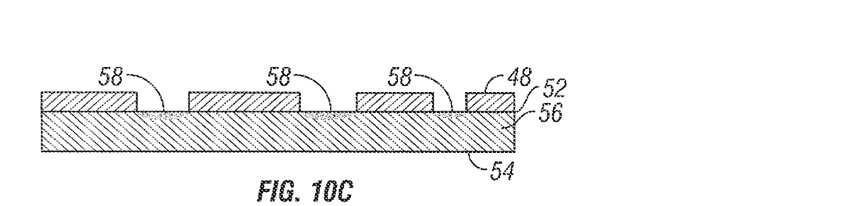

Referring to FIG. 10C, the implantable material 56 covered with the mask 48 is then illuminated by the ultraviolet rays. Because $TiO_2$ is sensitive to ultraviolet, the chemical composition in holes 58 is different from the area that is covered by the mask. In contrast to the geometric features illustrated in FIG. 9C, the geometric features 59 in FIG. 10C is not elevated relative to the surrounding surface of the implantable material.

Figure 10D:
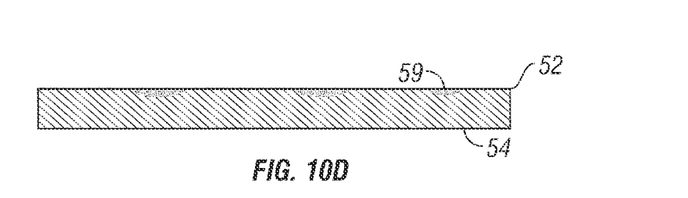

Referring to FIG. 10D, after ultraviolet irradiation, the mask is removed to reveal the surface 52 that surrounds the geometric features 59 formed by ultraviolet irradiation. As described above, because the shape of the holes 58 in the mask 48 could be in any of the shapes described for the geometric features including: circle, square, rectangle, triangle, parallel lines and intersecting lines, and combinations thereof, the geometric features 58 accordingly adopts such shapes also.

EXAMPLE 1

Nickel-titanium sheets were heated to oxidize titanium present at the surface of the sheet. Pattern masks fabricated from machined metal were laser drilled a pattern of holes having diameters ranging from 15 μm to 50 μm, with a single diameter of holes on each pattern mask. A single pattern mask was placed over a single nickel-titanium sheet and the assembly was exposed to high intensity ultra-violet irradiation. After UV irradiation, the irradiated nickel-titanium sheet was placed on a fully endothelialized test surface and maintained at 37° C. under simulated in vivo flow conditions and under static flow conditions. Qualitative observations were periodically made and it was found that endothelial cells bound to the pattern of UV irradiated affinity domains and migrated across the nickel-titanium sheet by proliferating across the pattern of affinity domains, eventually fully forming an endothelium on the nickel-titanium sheet.

What is claimed is:

1. An implantable, biocompatible material, wherein at least one surface of the biocompatible material has a plurality of functional features patterned on the at least one surface, wherein the endothelial cell binding affinity of each of the functional features is greater than the endothelial cell binding affinity of the rest of the surface of the biocompatible material, and wherein each of the functional features has a width between about 10 µm and about 75 µm.

2. The implantable, biocompatible material according to claim 1, wherein each of the functional features comprises photochemically altered regions of the biocompatible material.

3. The implantable, biocompatible material according to claim 2, wherein each of the photochemically altered regions comprises a titanium oxide.

4. The implantable, biocompatible material according to claim 1, wherein the biocompatible material comprises nickel-titanium alloy.

5. The implantable, biocompatible material according to claim 1, wherein each of the functional features is made of a material selected from the group consisting of carbon and nickel-titanium alloy.

6. The implantable, biocompatible material according to claim 1, wherein the functional features have a height between greater than 0µ to about 3.0µ.

7. The implantable, biocompatible material according to claim 1, wherein each of the functional features comprises a focal adhesion point for affinity binding of endothelial cells.

8. The implantable, biocompatible material according to claim 1, further comprising a gap distance between adjacent functional features between about 10 µm to about 75 µm.

9. An implantable, biocompatible material, comprising at least one original surface, wherein the at least one original surface has a patterned array of functional features on the at least one original surface that are at the same level as the surrounding original surface, wherein the patterned array of functional features has a surface energy that is different than the at least one original surface of the biocompatible material, wherein the different surface energy increases the rate of attachment of endothelial cells and the migration of endothelial cells relative to the original surface without the patterned array of functional features, and wherein each of the functional features has a width between about 10 µm and about 75 µm and a gap distance between adjacent functional features between about 10 µm and about 75 µm.

10. The implantable, biocompatible material according to claim 9, wherein each of the functional features comprises photochemically altered regions of the biocompatible material.

11. The implantable, biocompatible material according to claim 10, wherein each of the photochemically altered regions comprises a titanium oxide.

12. The implantable, biocompatible material according to claim 9, wherein the biocompatible material comprises nickel-titanium alloy.

13. The implantable, biocompatible material according to claim 9, wherein each of the functional features is made of a material selected from the group consisting of carbon and nickel-titanium alloy.

14. The implantable, biocompatible material according to claim 9, wherein each of the functional features comprises a focal adhesion point for affinity binding of endothelial cells.

15. An implantable, biocompatible material, wherein at least one surface of the biocompatible material has a plurality of functional features patterned on the at least one surface, wherein the endothelial cell binding affinity of each of the functional features is greater than the endothelial cell binding affinity of the rest of the surface of the biocompatible material, and wherein the gap distance between adjacent functional features is between about 10 µm and about 75 µm.

16. The implantable, biocompatible material according to claim 9, wherein each of the functional features comprises photochemically altered regions of the biocompatible material.

17. The implantable, biocompatible material according to claim 10, wherein each of the photochemically altered regions comprises a titanium oxide.

18. The implantable, biocompatible material according to claim 9, wherein the biocompatible material comprises nickel-titanium alloy.

19. The implantable, biocompatible material according to claim 9, wherein each of the functional features is made of a material selected from the group consisting of carbon and nickel-titanium alloy.

* * * * *